(12) United States Patent
Essawy et al.

(10) Patent No.: US 10,151,785 B2
(45) Date of Patent: Dec. 11, 2018

(54) PROBE HEATER REMAINING USEFUL LIFE DETERMINATION

(71) Applicant: Rosemount Aerospace Inc., Burnsville, MN (US)

(72) Inventors: Magdi A. Essawy, Lakeville, MN (US); James Joseph McTighe, Burnsville, MN (US); Ben Ping-Tao Fok, Rosemount, MN (US)

(73) Assignee: Rosemount Aerospace Inc., Burnsville, MN (US)

( * ) Notice: Subject to any disclaimer, the term of this patent is extended or adjusted under 35 U.S.C. 154(b) by 0 days.

(21) Appl. No.: 15/468,851

(22) Filed: Mar. 24, 2017

(65) Prior Publication Data

US 2018/0275182 A1    Sep. 27, 2018

(51) Int. Cl.
| | |
|---|---|
| *G01R 31/00* | (2006.01) |
| *H05B 3/44* | (2006.01) |
| *G01N 27/20* | (2006.01) |
| *G01N 27/24* | (2006.01) |
| *G01R 19/32* | (2006.01) |
| *G01N 27/02* | (2006.01) |

(Continued)

(52) U.S. Cl.
CPC .......... *G01R 31/008* (2013.01); *B64D 15/12* (2013.01); *B64D 45/00* (2013.01); *G01J 5/025* (2013.01); *G01N 27/026* (2013.01); *G01N 27/20* (2013.01); *G01N 27/24* (2013.01); *G01R 19/32* (2013.01); *H05B 3/44* (2013.01); *B64D 2045/0085* (2013.01); *G01J 2005/0077* (2013.01); *H05B 2214/02* (2013.01)

(58) Field of Classification Search
CPC .... G01R 31/008; G01R 19/32; G01N 27/026; G01N 27/24
See application file for complete search history.

(56) References Cited

U.S. PATENT DOCUMENTS

| | | | |
|---|---|---|---|
| 4,207,566 A | 6/1980 | Gitlin et al. | |
| 4,698,583 A | 10/1987 | Sandberg | |

(Continued)

FOREIGN PATENT DOCUMENTS

| | | |
|---|---|---|
| EP | 2755443 A2 | 7/2014 |
| EP | 3018057 A1 | 5/2016 |

(Continued)

OTHER PUBLICATIONS

Extended European Search Report for EP Application No. 18153825.7, dated May 4, 2018, 7 pages.

(Continued)

*Primary Examiner* — Walter L Lindsay, Jr.
*Assistant Examiner* — Milton Gonzalez
(74) *Attorney, Agent, or Firm* — Kinney & Lange, P.A.

(57) ABSTRACT

A probe system includes a heater and a control circuit. The heater includes a resistive heating element routed through the probe system. An operational voltage is provided to the resistive heating element to provide heating for the probe system. The control circuit is configured to provide the operational voltage and monitor a circuit frequency based on an element capacitance between the resistive heating element and a metallic sheath of the heater over time. The control circuit is further configured to determine remaining useful life of the probe system based on the circuit frequency.

17 Claims, 14 Drawing Sheets

(51) Int. Cl.
*G01J 5/02* (2006.01)
*B64D 15/12* (2006.01)
*B64D 45/00* (2006.01)
*G01J 5/00* (2006.01)

(56) References Cited

U.S. PATENT DOCUMENTS

| | | | |
|---|---|---|---|
| 5,464,965 A | 11/1995 | McGregor et al. | |
| 6,070,475 A * | 6/2000 | Muehlhauser | G01F 1/46 374/E13.006 |
| 6,151,560 A | 11/2000 | Jones | |
| 7,012,538 B2 * | 3/2006 | Peck | G01N 17/00 219/505 |
| 8,711,008 B2 * | 4/2014 | Cook | B64D 15/20 340/601 |
| 8,890,703 B2 | 11/2014 | Farris et al. | |
| 2004/0075567 A1 | 4/2004 | Peck et al. | |
| 2008/0018340 A1 | 1/2008 | Arnou et al. | |
| 2011/0290784 A1 | 12/2011 | Orawetz et al. | |
| 2014/0033175 A1 | 11/2014 | Macdonald | |
| 2015/0014303 A1 | 1/2015 | Köhler et al. | |
| 2015/0142343 A1 * | 5/2015 | Zach | G01N 25/00 702/57 |
| 2016/0013169 A1 | 5/2016 | Nesnidal | |

FOREIGN PATENT DOCUMENTS

| | | |
|---|---|---|
| WO | WO 90/11532 A1 | 10/1990 |
| WO | WO 9816837 A | 4/1998 |
| WO | WO 2011026740 A1 | 3/2011 |

OTHER PUBLICATIONS

Extended European Search Report for EP Application No. 18153822.4, dated May 14, 2018, 9 pages.
Extended European Search Report for EP Application No. 18153824.0, dated May 17, 2018, 9 pages.
Extended European Search Report for EP Application No. 181538301, dated May 23, 2018, 9 pages.
Extended European Search Report for EP Application No. 18153832.3 dated May 24, 2018, 9 pages.

* cited by examiner

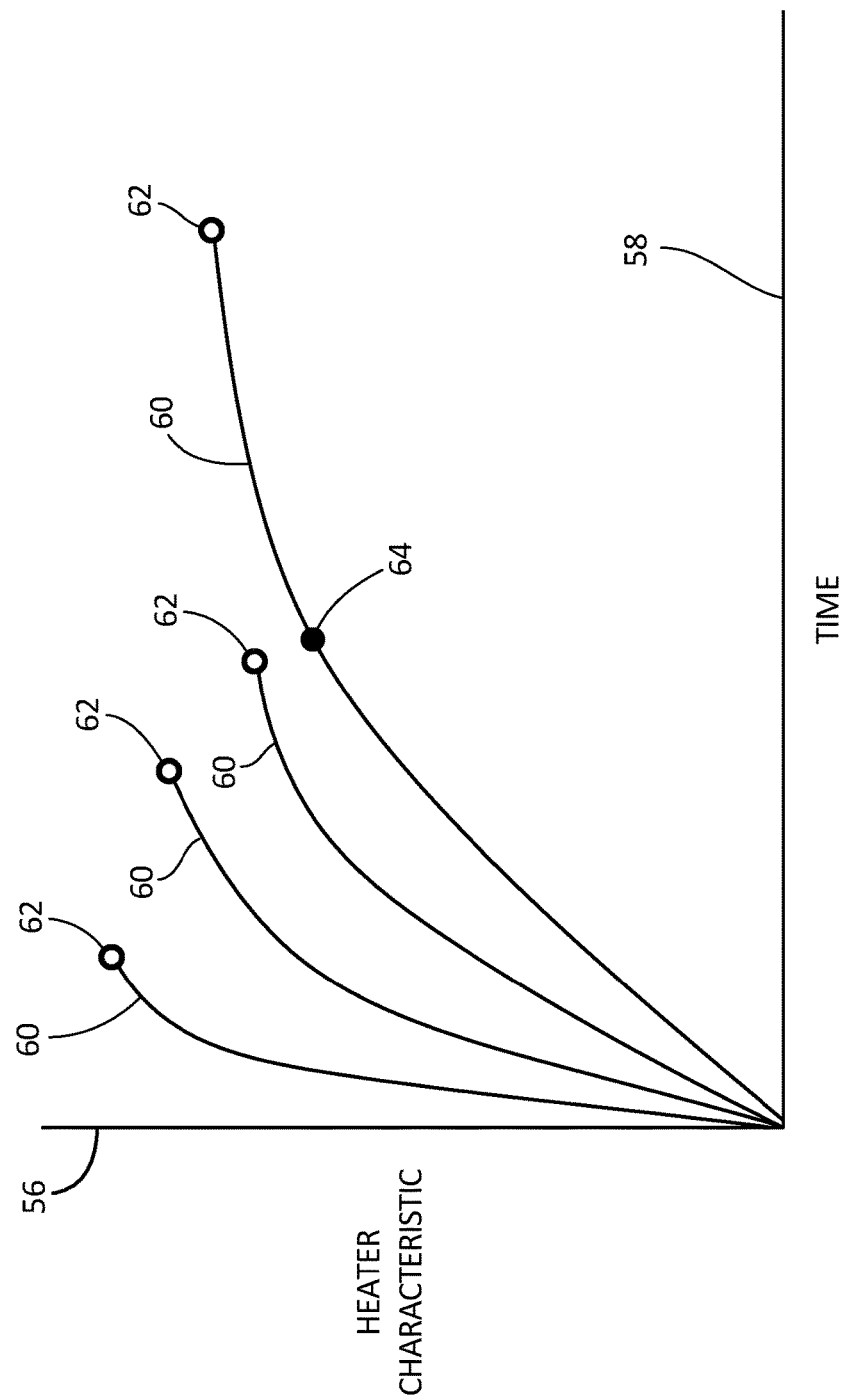

PROBE HEATER REMAINING USEFUL LIFE DETERMINATION

BACKGROUND

The present invention relates generally to probes, and in particular to a system and method for determining a remaining useful life of aircraft sensor probes.

Probes are utilized to determine characteristics of an environment. In aircraft systems, for example, probes may be implemented on the external portions of the aircraft to aide in determination of conditions such as airspeed, Mach number and flight direction, among others. Due to the harsh conditions of flight, ice may build-up on portions of the probe. To combat this, heaters are implemented within the probe to prevent the formation of ice that may impact proper functionality of the probe.

When probes break down, they need to be replaced, often prior to a subsequent takeoff. The heating element of a probe is often the most life-limited part. Therefore, probes need to be replaced as soon as the heating element breaks down. It is desirable to predict a remaining useful life of the probe heating element in order to better predict maintenance needs of the probe itself.

SUMMARY

A system for an aircraft includes a probe and a control circuit. The probe includes a heater comprising a resistive heating element routed through the probe. An operational voltage is provided to the resistive heating element to provide heating for the probe. The control circuit is configured to determine and monitor a circuit frequency based on an element capacitance between the resistive heating element and a metallic sheath of the heater over time. The control circuit is further configured to determine a remaining useful life of the probe based on the circuit frequency of the resistive heating element over time.

A method for determining a remaining useful life of a probe includes providing an operational voltage to a heater of the aircraft probe during a plurality of flights of an aircraft to provide heat for the probe, wherein the heater includes a resistive heating element and a metallic sheath; determining, by a control circuit, a circuit frequency based on an element capacitance between the resistive heating element and the metallic sheath during the plurality of flights; and determining the remaining useful life of the probe based upon the circuit frequency over time.

A probe system includes a heater and a control circuit. The heater includes a resistive heating element routed through the probe system. An operational voltage is provided to the resistive heating element to provide heating for the probe system. The control circuit is configured to provide the operational voltage and monitor a circuit frequency based on an element capacitance between the resistive heating element and a metallic sheath of the heater over time. The control circuit is further configured to determine remaining useful life of the probe system based on the circuit frequency.

BRIEF DESCRIPTION OF THE DRAWINGS

FIG. 4 is chart illustrating functions of a monitored characteristic of a plurality of probe heating elements over time.

DETAILED DESCRIPTION

A system and method for determining the remaining useful life of a probe is disclosed herein that includes monitoring characteristics of the probe over time. The probe, which may be an aircraft total-air-temperature (TAT) probe or any other probe, includes a resistive heating element, such as a heater wire, routed through the probe. Over time, as the heater wire ages, the heater wire may degrade, causing characteristics of the heater wire to change. These changing characteristics may be monitored and plotted over time, for example. The remaining useful life of the probe may then be determined and reported based upon the monitored characteristics.

Figure 1:
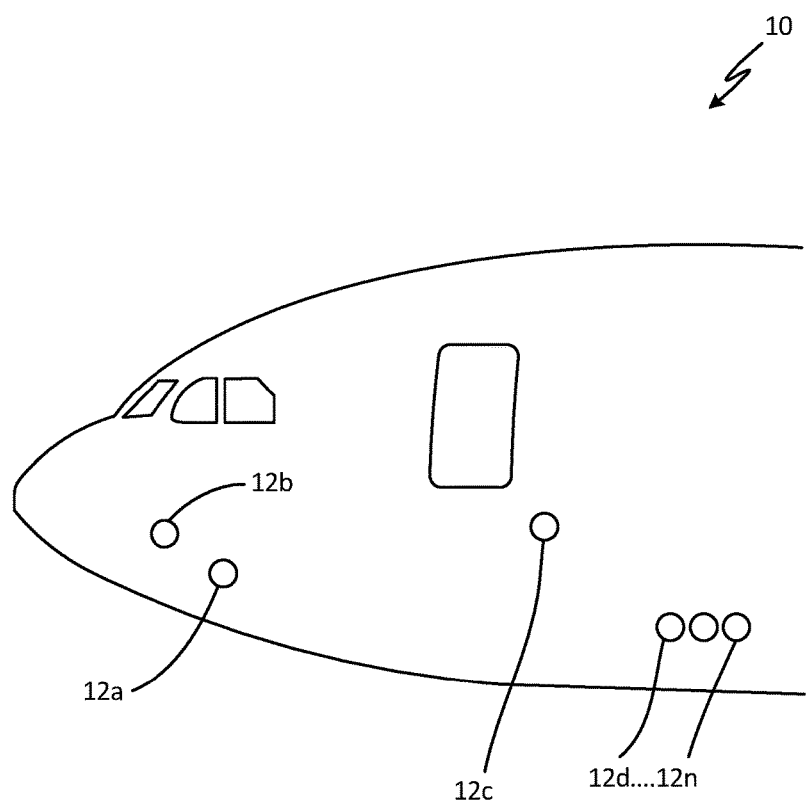
FIG. 1 is a diagram illustrating an aircraft that includes a plurality of probes.

FIG. 1 is a diagram illustrating aircraft 10 that includes a plurality of probes 12a-12n. While illustrated as a commercial aircraft, other vehicles, such as unmanned aerial vehicles, helicopters and ground vehicles may also include probes 12a-12n configured to sense characteristics of the environment. Probes 12a-12n may be any type of probe such as, but not limited to, pitot probes, TAT probes, angle-of-attack (AOA) probes and any other probes that may include a resistive heating element.

Figure 2:
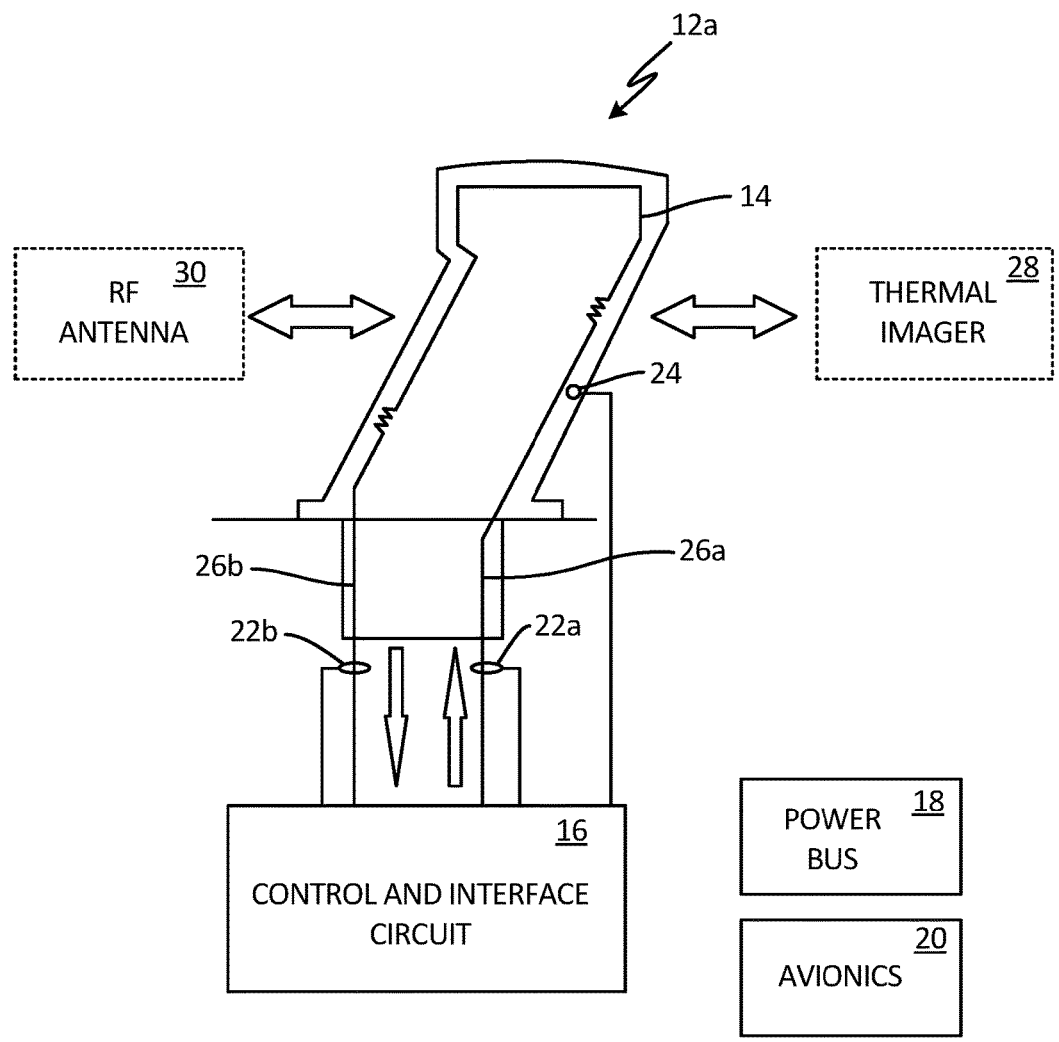
FIG. 2 is a diagram of an aircraft probe that includes a heating element.

FIG. 2 illustrates aircraft probe 12a that includes resistive heating element 14. While illustrated in FIG. 2 as a TAT probe 12a, aircraft probe 12a may be any other type of probe 12a-12n or sensing element. Probe 12a is connected to receive control and power from control and interface circuit 16. Control and interface circuit 16 may be implemented local to probe 12a (e.g., implemented as a "smart probe") or remote of probe 12a. Control and interface circuit 16 may include, for example, a microcontroller, programmable logic device, application integrated circuit (ASIC), or any other digital and/or analog circuitry.

Resistive heating element 14, which may be a heater wire, for example, may receive power directly, or through control and interface circuit 16, from aircraft power bus 18 to provide heating for probe 12a. Power bus 18 may be any direct current (DC) or alternating current (AC) aircraft power bus. For example, resistive heating element 14 may receive power from a 28 Volt DC power bus. An operational current, based on the power received from power bus 18, flows through resistive heating element 14, which provides heating for probe 12a. Control and interface circuit 16 may also be connected to aircraft avionics 20. Alternatively, control and interface circuit 16 may be implemented integral to aircraft avionics 20. Control and interface circuit 16 may be configured to provide data to, and receive data from, aircraft avionics 20.

Current sensors 22a and 22b may sense current flowing into, and out of, resistive heating element 14 at heating element input 26a and heating element output 26b, respectively. Current sensors 22a and 22b may provide a signal indicative of the sensed current at the respective locations to control and interface circuit 16. Temperature sensor 24 may be positioned to sense a temperature of probe 12a and provide the sensed temperature to control and interface circuit 16. In other embodiments, a temperature may be estimated, for example, based upon sensed aircraft conditions and provided to control and interface circuit 16 from avionics 20. For example, avionics 20 may determine a present altitude and/or airspeed of aircraft 10 and may estimate the temperature of probe 12a based upon, among other items, the present altitude and/or airspeed. Current sensors 22a and 22b may be any devices that sense current. In an embodiment, current sensors 22a and 22b may be non-contact current sensors such as, for example, a current transformer or Hall effect sensor.

Thermal imager 28 may be located integral to, or separate from, aircraft 10. Thermal imager 28 may be any device capable of receiving infrared radiation, for example, and providing an electrical output indicative of the received infrared radiation. While not illustrated as such, thermal imager 28 may be connected to communicate with control and interface circuit 16 and/or avionics 20 through a wired or wireless connection. This way, thermal images of probe 12a may be obtained, analyzed and stored over time.

Radio-frequency (RF) antenna 30 is any antenna structure capable of emitting and/or receiving an RF signal. RF antenna 30 may be configured to receive power and emit RF radiation that may be received by heating element 14, for example. Heating element 14, which may include a large loop of heater wire having dielectric properties, may act as an antenna, capable of emitting and/or receiving RF energy. RF antenna 30 may be located integral to, or separate from, aircraft 10. RF antenna 30 may be connected to communicate with control and interface circuit 16 and/or avionics 20 through a wired or wireless connection (not shown). This way, control and interface circuit 16 may control RF antenna 30 to emit a plurality of RF signal frequencies, and/or may analyze a response of RF antenna 30 to an RF signal emitted by heater wire 14, for example.

Over time, resistive heating element 14 may degrade, and eventually break down such that current may no longer flow through resistive heating element 14 to provide heating for probe 12a. Once resistive heating element 14 has broken down, aircraft probe 12a must be repaired or replaced. A TAT probe, for example, may be utilized, among other things, to determine a Mach number for the aircraft. The Mach number may be needed for takeoff and thus, the TAT probe may be required to be functional prior to taking off. If the TAT probe is malfunctioning, it must be replaced, which may cause undesirable flight delays. If the remaining useful life of the TAT probe is known, the TAT probe can be replaced between flights or at another convenient time for repair, preventing delays or other costs incurred due to an unexpected failure of the probe.

Figure 3:
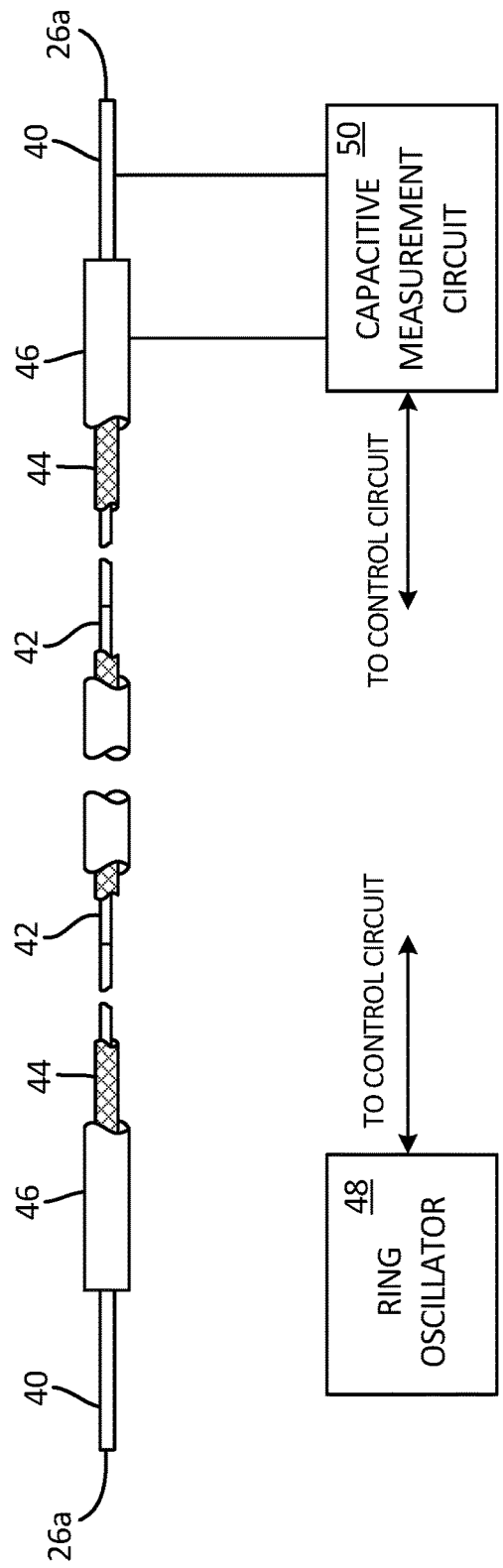
FIG. 3 is a diagram illustrating a heating element of an aircraft probe.

FIG. 3 is a diagram illustrating an embodiment of heating element 14 of aircraft probe 12a. Heating element 14, which is shown as a heater wire in the embodiment illustrated in FIG. 3, includes lead wire 40, heater element 42, insulation 44 and sheath casing 46. Sheath casing 46 may be a metallic sheath and thus, there may be a measurable capacitance between sheath casing 46 and lead wire 40. Ring oscillator 48 may be any oscillator circuit in which a capacitance may be utilized to drive an output frequency, for example. Capacitive measurement circuit 50 is any circuit capable of providing a value to control and interface circuit 16, for example, that allows control and interface circuit 16 to determine the capacitance between sheath casing 46 and lead wire 40. For example, capacitive measurement circuit 50 may be a resistor-capacitor (RC) or resistor-inductor-capacitor (RLC) circuit connected such that the capacitor for the RC or RLC circuit is the capacitance between lead wire 40 and metallic sheath 46. In some embodiments, ring oscillator 48 and capacitive measurement circuit 50 may be the same circuit.

During operation of probe 12a, changes may occur, for example, due to hot and cold cycles as well as other varying environmental conditions such as temperature, pressure, humidity, environmental gases and aerosols, among others. These environmental conditions, in addition to the temperature cycling of probe 12a, may cause a sealing of heating element 14 to become compromised, leading to foreign material leaking into insulation 44 and heater element 42. Heating element 14 may be oxidized and the dielectric material properties of heating element 14 may change. This may lead to certain characteristics of heating element 14 such as resistance and the capacitance between wire 40 and metallic sheath 46, among other characteristics, to change over time.

FIG. 4 illustrates functions 60 of a monitored characteristic over the life of several resistive heating elements 14 of several respective probes 12a-12n until breakdown 62. A heater wire, for example, may degrade as the heater wire ages. This degradation may cause changes in characteristics of heater wire 14 such as resistance and capacitance. For example, the current drawn through resistive heating element 14 may increase monotonically over the life of heating element 14. This increase is not linear, but rather follows exponential function 60, with a point 64 of interest. Point 64 may be the point on function 60, for example, at which the slope transitions from greater than 1 to less than 1. While the maximum normalized characteristic and life of each resistive heating element 14 at breakdown 62 may fluctuate, exponential function 60 of the heater characteristic over the life of each resistive heating element 14 remains similar.

Functions 60 shown in FIG. 4 may be obtained, for example, through testing of probes 12a-12n. For a selected characteristic of heating element 14, such as current draw, capacitance, leakage current, thermal response, or other characteristic, function 60 may be determined through the testing of probes 12a-12n. Current may be cycled, for example, until heating element 14 of a respective test probe 12a-12n breaks down. A characteristic of heating element 14 may be monitored each test cycle and plotted over time until breakdown 62. The plots of the characteristic may then be utilized to determine function 60. Function 60 may then be utilized during normal operation of a probe 12a-12n to determine, for example, a half-life estimate of heating element 14. In other embodiments, other algorithms may be utilized to determine the remaining useful life of heating element 14 based upon the plotted data.

In an example embodiment, current may be sampled using current sensor 22a or 22b at any time during flight and provided to control and interface circuit 16 several times each flight. This sampled current may be stored in a memory of control and interface circuit 16, for example, or some other memory or storage device. Because current is directly affected by temperature, a temperature may also be sensed using temperature sensor 24 and stored along with a respective sensed current so that the current may be normalized with respect to temperature. Alternatively, a temperature may be estimated using data from avionics 20, for example. Control and interface circuit 16 may utilize the sensed or estimated temperature to directly normalize the current prior to storage, or may store the two values for later normalization.

Function 60, determined during testing, may be used in conjunction with the stored normalized current to determine the half-life estimate of heating element 14. For example, the stored normalized current may be plotted by control and interface circuit 16 such that a present slope of the plot may be determined. This present slope may be utilized, for example, to detect point 64 by detecting that the slope of the plot has transitioned from greater than 1 to less than 1, or any other point on function 60. Once point 64 is detected, for example, the half-life of heating element 14 may be determined.

Figure 5A:
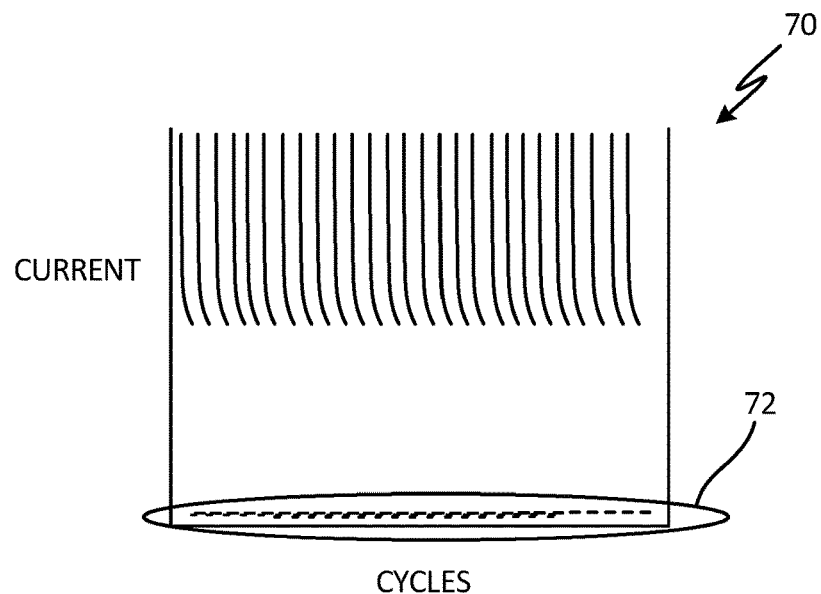
FIGS. 5A and 5B are charts illustrating monitored current based on a low voltage for a heating element over time.
Figure 5B:
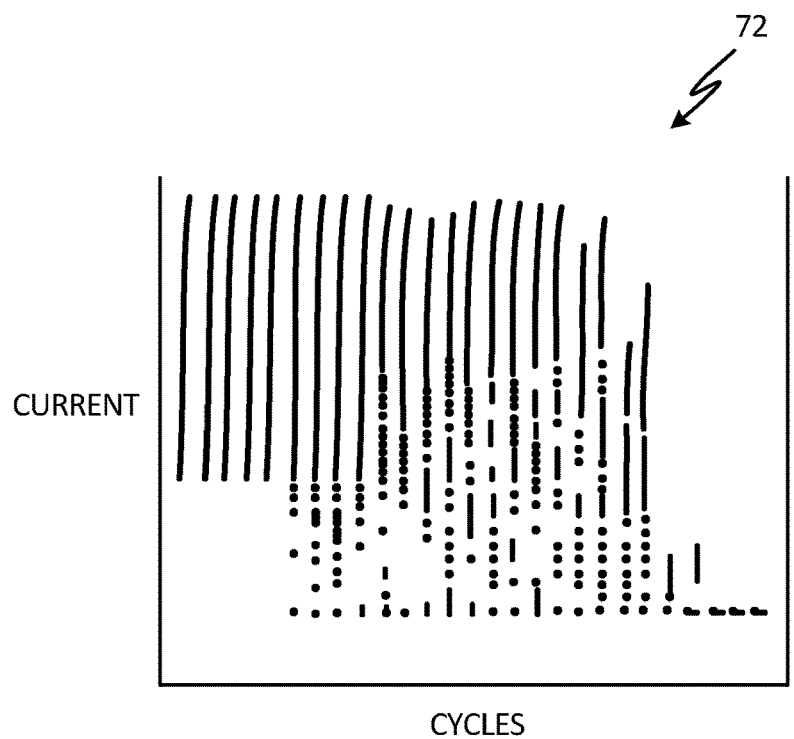

FIGS. 5A and 5B are charts illustrating monitored current based upon a normal operating voltage and a low voltage for heating element 14 over time. FIG. 5A illustrates both a current draw 70 for an operating voltage and current draw 72 for a low voltage. FIG. 5B shows a zoomed in view of current draw 72 for a low voltage. In an embodiment, the operating voltage may be, for example, 28 Volts while the low voltage may be, for example, 0.1 Volts.

At the end of the life of heating element 14, thermal fatigue causes heater wire 40 to fracture and gradually become electrically open, which increases the resistance of heating element 14. At low voltage, electron tunneling is the main mechanism for electrical current conduction. Arcing that occurs at 0.1 Volts may indicate a micro fracture with a gap on the order of 1 nanometer (nm), while arcing that occurs at 28 Volts may correspond to an approximately 0.3 micrometer (um) gap. Thus, micro fractures may be detected by monitoring a current response using a low voltage prior to failure of heating element 14.

As seen in FIG. 5A, the current drawn during normal operation (e.g., receiving 28 Volts from power bus 18) remains substantially greater than zero over all cycles. As seen in FIG. 5B, the current drawn with 0.1 Volts begins to degrade to, and remain at, zero while the current drawn during normal operation continues to be substantially greater than zero. This degradation of current to zero at low voltage indicates that a micro fracture is present in heating element 14. This micro fracture may eventually grow in size, ultimately causing failure of probe 12a. By detecting these micro fractures early, failure of probe 12a may be predicted such that a remaining useful life of heating element 14, and in turn, probe 12a, may be determined.

The amount of remaining useful life of probe 12a following detection of a micro fracture may be determined, for example, through testing of probes 12a-12n. Current may be cycled, for example, until heating element 14 of a respective test probe 12a-12n breaks down. Between test cycles, a low voltage may be provided to test probes 12a-12n. While the low voltage is supplied, a current may be sensed and stored. This way, the cycle at which a micro fracture on the order of 1 nm is detected may be determined. Following detection of the micro fracture, once the respective test probe 12a-12n breaks down, a percentage of life after detection of the micro fracture may be determined.

During normal operation of probes 12a-12n, a low voltage may be provided, for example, by control and interface circuit 16 between flights of aircraft 10, or at any other time during which heating element 14 is not receiving an operational voltage. Current sensor 22a or 22b may be utilized by control and interface circuit 16 to obtain a sensed current while providing the low voltage. Upon detection of the sensed current going to zero at low voltage, a remaining useful life may be determined based upon the percentage of life determined during testing of the probes 12a-12n.

Figure 6:
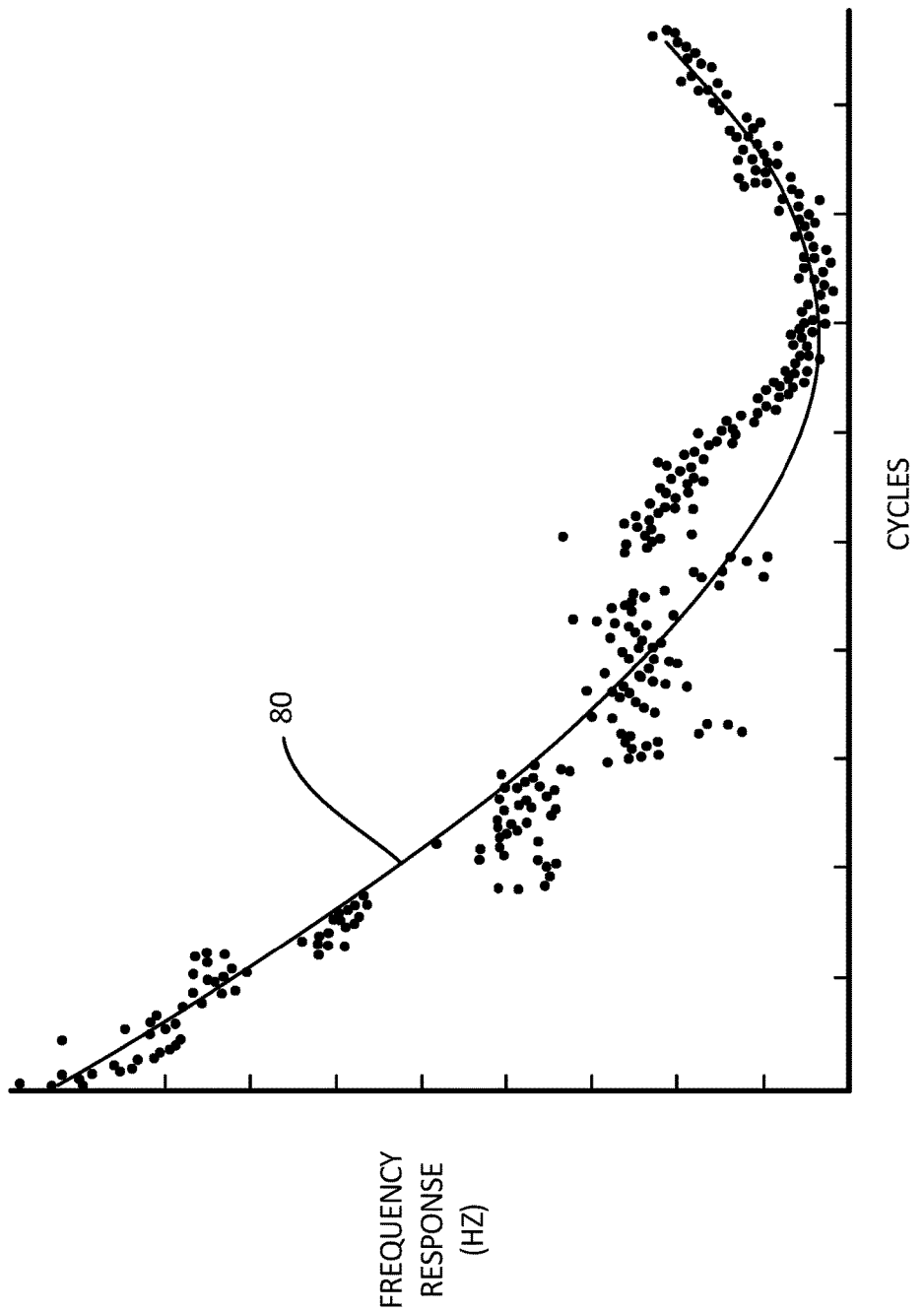
FIG. 6 is a chart illustrating a resonant frequency over time for a heating element of an aircraft probe.

FIG. 6 is a chart illustrating a resonant frequency over time for heating element 14 of aircraft probe 12a. FIG. 6 also illustrates a curve 80 fit to the resonant frequency plot over time. As seen in FIG. 3, a capacitance exists between metallic sheath 46 and lead wire 40. While in operation, changes to heating element 14 happen due to hot and cold cycles in addition to varying environmental conditions such as temperature, pressure, humidity, environmental gases, and aerosols, among others. These conditions, in addition to the temperature cycling of probe 12a, cause the probe heater sealing to be compromised, which may lead to various materials leaking into insulation 44 and heater element 42. Wire 40 may be oxidized and dielectric material properties may change, leading to a change in capacitance and resistance of heating element 14. Because the capacitance changes, the resonant frequency also changes.

In an embodiment, to obtain the resonant frequency, the capacitance between metallic sheath 46 and lead wire 40 may be swept with frequencies ranging from 1 kilohertz (KHz) to 100 megahertz (MHz) by control and interface circuit 16, for example, through capacitive measurement circuit 50. The peak frequency response and bandwidth may be identified by control and interface circuit 16. This peak frequency response may be monitored and stored over time and plotted as shown in FIG. 6. In one embodiment, a function 80 obtained during testing of probes 12a-12n, for example, may then be utilized in conjunction with the stored and plotted resonant frequency to determine a remaining useful life of probe 12a. For example, it may be determined when the slope of the plotted resonance transitions from greater than −1 to less than −1, or when the slope transitions from a negative value to a positive value, as seen in FIG. 6. Determination of a present point on function 80 allows control and interface circuit 16 to determine a remaining useful life of probe 12a.

In another embodiment, algorithms that separate data indicative of a healthy probe and data indicative of an increasingly unhealthy probe may be executed utilizing various signal processing techniques to determine the remaining useful life of heating element 14. For example, time-frequency analysis, machine learning, index theory and other signal processing techniques may be utilized to determine remaining useful life of heating element 14 based upon the monitored resonant frequency.

In another embodiment, ring oscillator 48 may be utilized with probe 12a as the driving element of the output frequency of ring oscillator 48. Ring oscillator 48, or other oscillator circuit, has an output frequency dependent upon the structure of the circuit and the input voltage to the circuit.

By controlling the input voltage, the output frequency of ring oscillator 48 can be made dependent solely upon the capacitance between metallic sheath 46 and lead wire 40. As this capacitance changes as heating element 14 degrades, so does the output frequency of ring oscillator 48. The changing output frequency may be stored and plotted over time to determine a remaining useful life of probe 12a. For example, testing of probes 12a-12n may result in a function of the output frequency similar to that shown in FIG. 4 or 6. This function, in conjunction with the stored and plotted output frequency, may be utilized to determine the remaining useful life of probe 12a during normal operation.

In another embodiment, RF antenna 30 may be controlled to sweep a wide range of frequencies. For example, control and interface circuit 16 may provide AC power to antenna 30 at varying frequencies to facilitate emission of RF radiation at a plurality of frequencies from antenna 30. The S12 parameter for heating element 14, which is a measure of the power received at heating element 14 from the RF emission of antenna 30, may be determined and monitored by control and interface circuit 16.

This antenna response of heating element 14 may be analyzed by control and interface circuit 16 to determine, for example, a resonant frequency response of heating element 14. The antenna properties of heating element 14 may be dependent upon, among other things, length and shape of heating element 14, and dielectric properties of heating element 14. These dielectric properties may include, for example, permittivity, permeability, homogeneity and thickness, among others. As the wire ages and degrades, the dielectric properties of heating element 14 may change, which may lead to a change in the resonant frequency of heating element 14.

The determined resonant frequency may be monitored and plotted over time by control and interface circuit 16. Testing of probes 12a-12n may be utilized to determine a function at which the resonant frequency changes over time. This function may substantially follow those shown in FIG. 4 or 6, for example. This function may then be utilized to determine, for example, a half-life of heating element 14 base upon the determined resonant frequency during normal operation of probe 12a. In other embodiments, an algorithm may be executed using signal processing techniques to determine the remaining useful life of probe 12a based upon the resonant frequency changes over time.

In another embodiment, control and interface circuit 16 may provide AC power to heating element 14 at varying frequencies to facilitate emission of RF radiation at a plurality of frequencies from heating element 14. Control and interface circuit 16 may then monitor the S12 parameter of RF antenna 30 to determine a resonant frequency, which may be monitored and analyzed over time to determine a half-life of heating element 14.

Figure 7A:
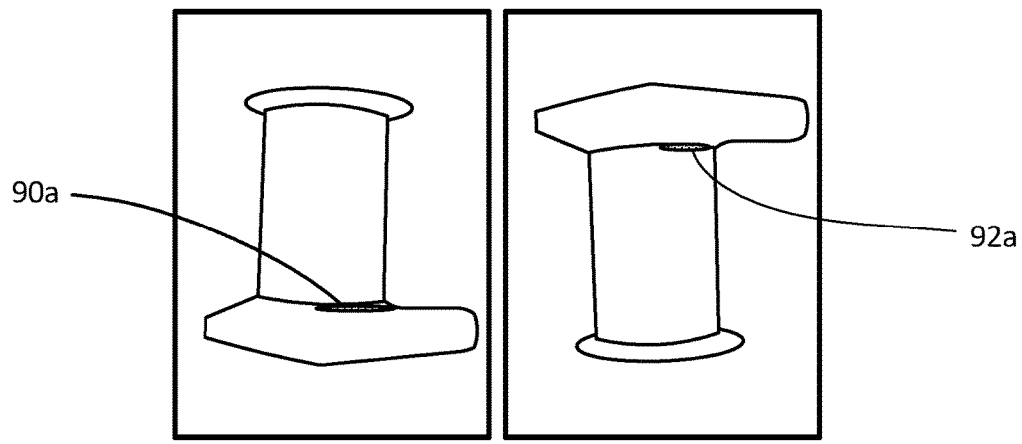
FIGS. 7A and 7B are thermal images of an aircraft probe.
Figure 7B:
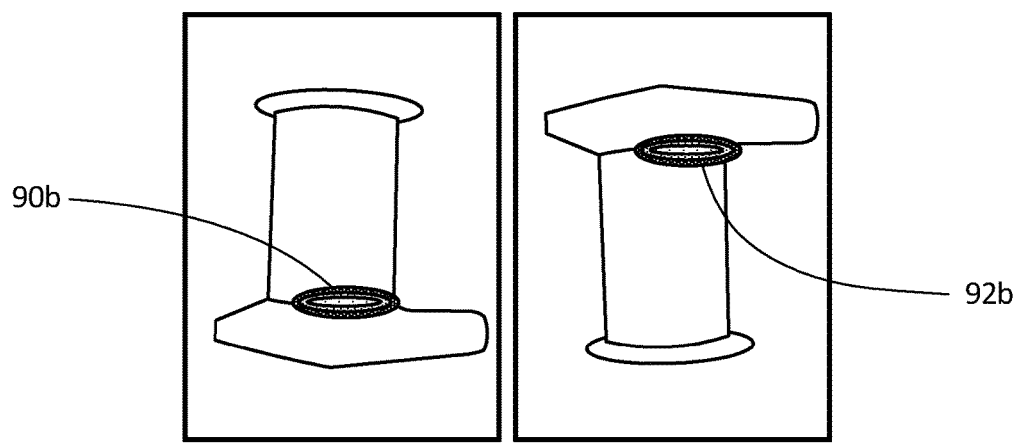

FIGS. 7A and 7B are representatives of thermal images of aircraft probe 12a. These images may be obtained, for example, using thermal imager 28 (FIG. 2). FIG. 7A illustrates probe 12a at a beginning of its lifetime, while FIG. 7B illustrates probe 12a at a later point in its lifetime. The thermal images may be utilized, for example, to determine a thermal response of heating element 14 over time. Points of interest 90a and 92a show a thermal response of heating element 14 at the beginning of life of heating element 14, while points of interest 90b and 92b show a thermal response of heating element 14 at a later point in life. While illustrated as images captured at various view angles with respect to probe 12a, any number of thermal images at any angle with respect to probe 12a may be obtained by imager 28. Other points of interest for heating element 14 may also be monitored separately, or in conjunction with, points 90a, 90b, 92a and 92b to determine the thermal response of heating element 14.

As seen in FIG. 7B, the temperature at points 90b and 92b of heating element 14 has increased from the temperature at points 90a and 92a shown in FIG. 7A. This increase may be due to changes in heating element caused by degradation of heating element 14 over time. The increase in temperature over time may substantially follow an exponential function similar to those illustrated in FIG. 4. Because of this, the thermal response of heating element 14 (e.g., the increase in temperature seen at points 90b and 92b) may be stored and plotted over time during normal operation of probe 12a. An exponential function determined during testing of probes 12a-12n, for example, may then be used in conjunction with the stored and plotted thermal response to determine a half-life of heating element 14.

Figure 8:
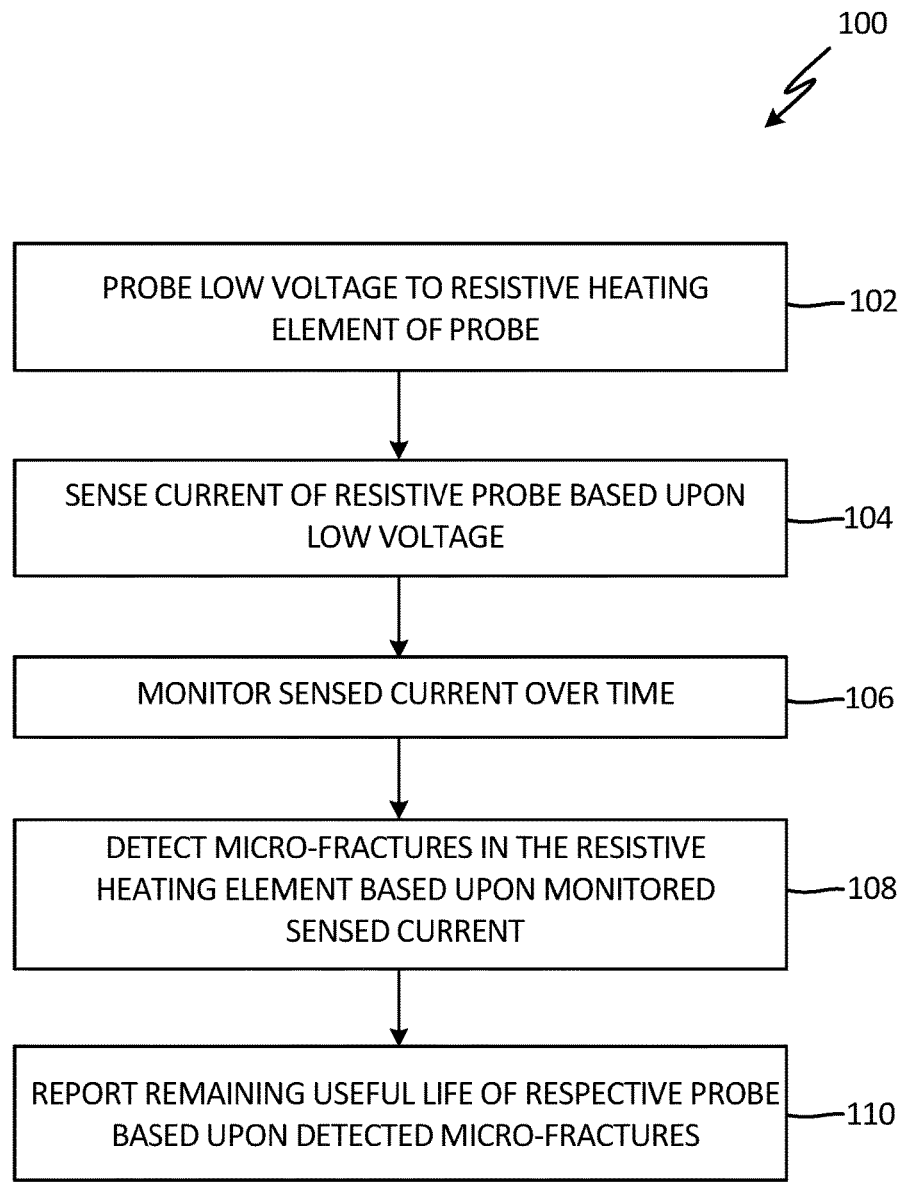
FIG. 8 is a flowchart illustrating a method of determining a remaining useful life of a probe based upon detected micro-fractures.

FIG. 8 is a flowchart illustrating method 100 of determining a remaining useful life of probe 12a based upon detected micro-fractures. At step 102, a low voltage is provided to heating element 14 of probe 12a. This low voltage may be provided at any time, such as right after power down of probe 12a. The low voltage may be approximately 0.1 V, which may be low enough to detect micro fractures on the order of 1 nm.

A step 104, while the low voltage is being supplied to heating element 14, current is sensed by one of current sensors 22a and 22b. The sensed current may be provided to, and stored by, control and interface circuit 16. The process in steps 102 and 104 is repeated over time, and the sensed current is monitored by control and interface circuit 16 at step 106. At step 108, micro fractures in heating element 14 are detected based upon the monitored current. For example, if the monitored current has dropped to zero, as illustrated in FIG. 5B, a micro fracture is detected by control and interface circuit 16.

Following detection of an approximately 1 nm micro fracture, the remaining useful life of heating element 14 may be estimated. This estimation may be based upon testing of heating elements 14, for example. Probes 12a-12n may be tested to determine an average remaining useful life of heating element 14 following detection of a micro fracture of approximately 1 nm.

Once the remaining useful life of resistive heating element 14 is determined by control and interface circuit 16, the remaining useful life may be reported at step 110. This report may be made to the cockpit through avionics 20, or to some other computer system. By reporting the remaining useful life, probes 12a-12n may be replaced prior to breaking down and thus, unnecessary flight delays may be avoided.

Figure 9:
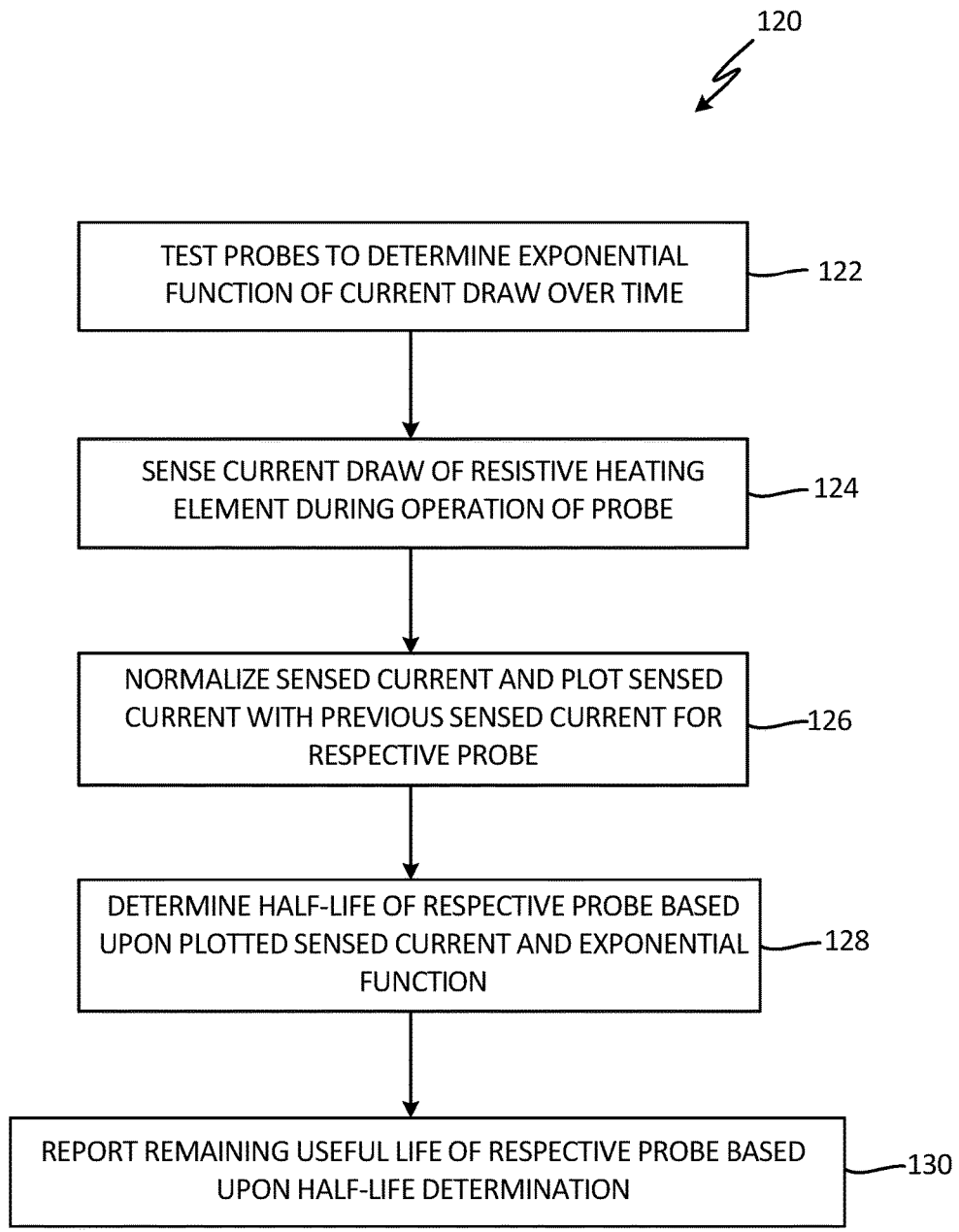
FIG. 9 is a flowchart illustrating a method of determining a remaining useful life of a probe based upon a monitored current draw over time by a heating element of a probe.

FIG. 9 is a flowchart illustrating method 120 of determining a remaining useful life of a probe 12a-12n based upon monitored current drawn over time by a respective heating element 14. At step 122, an exponential function for a respective probe 12a-12n may be determined, for example, through testing of similar probes 12a-12n. The test probes may have a test current provided to a respective resistive heating element 14 during a plurality of test cycles. The current may be sensed at common points during each of the plurality of test cycles and the sensed currents may then be plotted and functions 60 may be determined as shown in FIG. 4 for the respective resistive heating elements 14. This exponential function may then be used for all similar probes 12a-12n during normal probe operation in order to determine a half-life of a respective resistive heating element 14, for example.

During normal operation of probes 12a-12n, current through resistive heating element 14 may fluctuate based upon the operating point of probe 12a-12n. Therefore, it may be desirable at step 124 to sense the operational current at a similar point of operation of heating element 14. For example, upon initial power-on of resistive heating element 14, the current may rise to a peak current. As resistive heating element 14 increases in temperature, the current through resistive heating element 14 will decrease to a lower, steady-state current. Thus, current may be sampled and stored consistently at the peak value, at the steady-state value, or at some other expected value, for example.

Temperature may also be sensed and provided to control and interface circuit 16 using temperature sensor 24. At step 126, control and interface circuit 16 may normalize the sensed current using the sensed temperature. Steps 124 and 126 may be repeated and the normalized sensed current may be plotted over several flights, for example, to establish a curve fit. The curve fit may substantially follow the exponential function determined, for example, at step 122. At step 128, the present slope of the sensed current may be determined based upon the exponential function. This slope may then be utilized to determine the half-life of resistive heating element 14. By knowing the half-life of resistive heating element 14, the remaining useful life of resistive heating element 14 may be determined by control and interface circuit 16, for example.

Once the remaining useful life of resistive heating element 14 is determined by control and interface circuit 16, the remaining useful life may be reported at step 130. This report may be made to the cockpit through avionics 20, or to some other computer system. By reporting the remaining useful life, probes 12a-12n may be replaced prior to breaking down and thus, unnecessary flight delays may be avoided.

Figure 10:
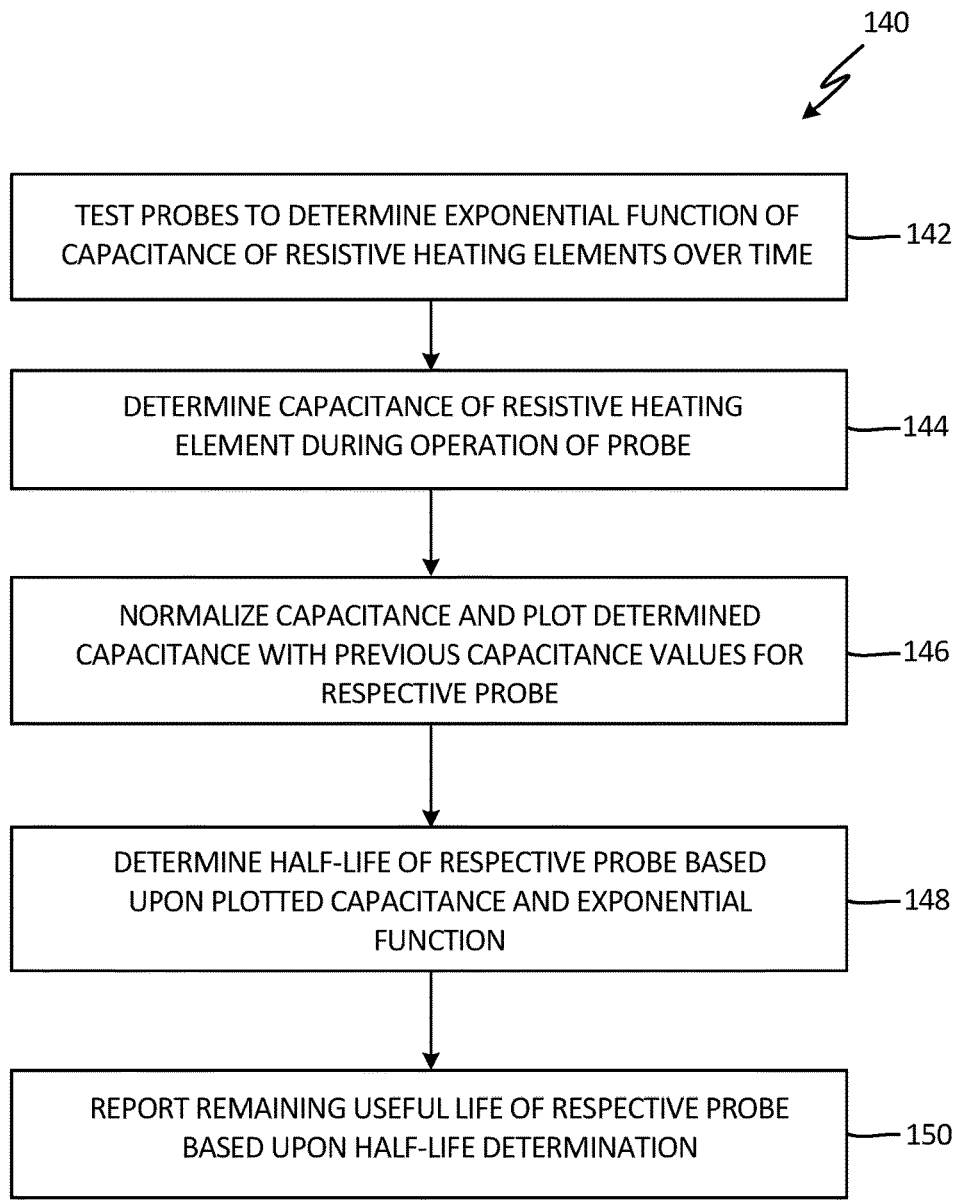
FIG. 10 is a flowchart illustrating a method of determining a remaining useful life of a probe based upon a determined capacitance of a heating element of a probe.

FIG. 10 is a flowchart illustrating method 140 of determining a remaining useful life of probes 12a-12n based upon a determined capacitance of a respective heating element 14. At step 142, an exponential function for a respective probe 12a-12n may be determined, for example, through testing of similar test probes. The test probes may have a test current provided to a respective resistive heating element 14 during a plurality of test cycles to simulate the life of the respective probe 12a-12n. The current may be cycled until failure of each respective probe 12a-12n. The capacitance of each respective heating element 14 may be determined during each cycle, for example. An exponential function, such as those shown in FIG. 4, may be determined based upon the determined capacitances. This exponential function may then be used for all similar probes 12a-12n during normal probe operation in order to determine a half-life of a respective resistive heating element 14, for example.

At step 144, during normal operation of probes 12a-12n, capacitive measurement circuit 50 may be utilized to determine a capacitance between metallic sheath 46 and lead wire 40. The capacitance and capacitance measurement circuit 50 may be directly affected by temperature. At step 146, temperature may be sensed and provided to control and interface circuit 16 using temperature sensor 24. Steps 144 and 146 may be repeated throughout the life of probe 12a and control and interface circuit 16 may normalize the determined capacitance using the sensed temperature and may plot the normalized determined capacitance over several flights, for example, to establish a curve fit. The curve fit may substantially follow the exponential function determined, for example, at step 142. At step 148, the present slope of the determined capacitance may be determined based upon the exponential function. This slope may then be utilized to determine the half-life of resistive heating element 14. By knowing the half-life of resistive heating element 14, the remaining useful life of resistive heating element 14 may be determined by control and interface circuit 16, for example.

Once the remaining useful life of resistive heating element 14 is determined by control and interface circuit 16, the remaining useful life may be reported at step 150. This report may be made to the cockpit through avionics 20, or to some other computer system. By reporting the remaining useful life, probes 12a-12n may be replaced prior to breaking down and thus, unnecessary flight delays may be avoided.

Figure 11:
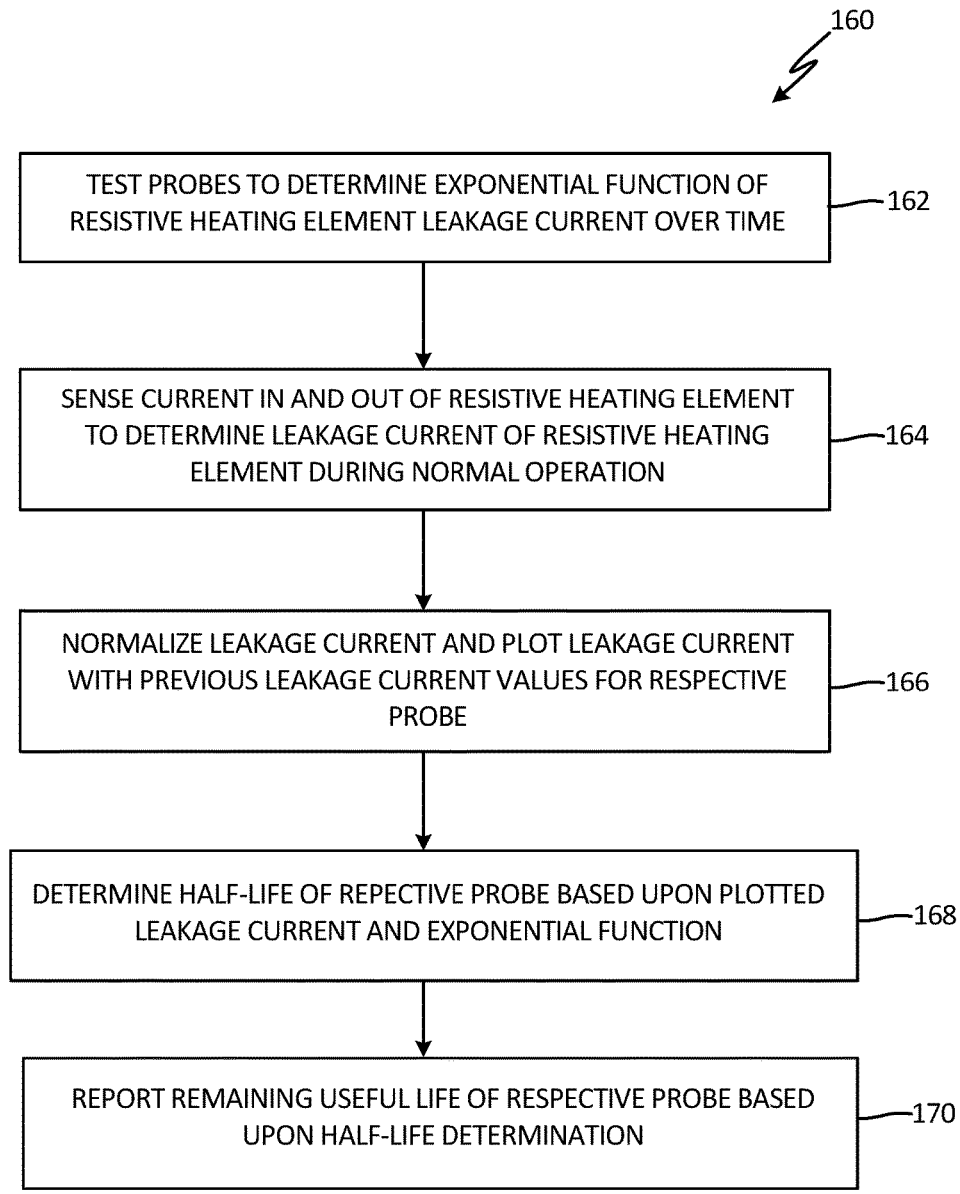
FIG. 11 is a flowchart illustrating a method of determining a remaining useful life of a probe based upon current leakage of a heating element of the probe.

FIG. 11 is a flowchart illustrating method 160 of determining a remaining useful life of probes 12a-12n based upon a measured leakage current for a respective heating element 14. At step 162, an exponential function for a respective probe 12a-12n may be determined, for example, through testing of similar probes 12a-12n. The test probes may have a test current provided to a respective resistive heating element 14 during a plurality of test cycles to simulate the life of the respective probe 12a-12n. Current may be sampled by both current sensors 22a and 22b and provided to control and interface circuit 16. The current from current sensor 22b for example, may be subtracted from the current from current sensor 22a to determine a leakage current of resistive heating element 14. The current may be cycled until failure of each respective probe 12a-12n at which time the exponential function, similar to those illustrated in FIG. 4, may be determined.

At step 164, during normal operation of probes 12a-12n, leakage current from resistive heating element 14 may be determined based upon sensed current from both current sensors 22a and 22b. Current through resistive heating element 14 may fluctuate based upon the operating point of probe 12a-12n. Therefore, it may be desirable to determine the leakage current at a similar point of operation of heating element 14 each time the current is sensed and stored. For example, upon initial power-on of resistive heating element 14, the current may rise to a peak current. As resistive heating element 14 increases in temperature, the current through resistive heating element 14 will decrease to a lower, steady-state current. Thus, current may be sampled and stored consistently at the peak value, at the steady-state value, or at some other expected value, for example.

Temperature may also be sensed and provided to control and interface circuit 16 using temperature sensor 24. At step 166, control and interface circuit 16 may normalize the determined leakage current using the sensed temperature. Steps 164 and 166 may be repeated and control and interface circuit 16 may plot the normalized leakage current over several flights, for example, to establish a curve fit. The curve fit may substantially follow the exponential function determined, for example, at step 162. At step 168, the present slope of the determined leakage current may be determined based upon the exponential function. This slope may then be utilized to determine the half-life of resistive heating element 14. By knowing the half-life of resistive heating element 14, the remaining useful life of resistive heating element 14 may be determined by control and interface circuit 16, for example.

Once the remaining useful life of resistive heating element 14 is determined by control and interface circuit 16, the remaining useful life may be reported at step 170. This report may be made to the cockpit through avionics 20, or to some other computer system. By reporting the remaining useful life, probes 12a-12n may be replaced prior to breaking down and thus, unnecessary flight delays may be avoided.

Figure 12:
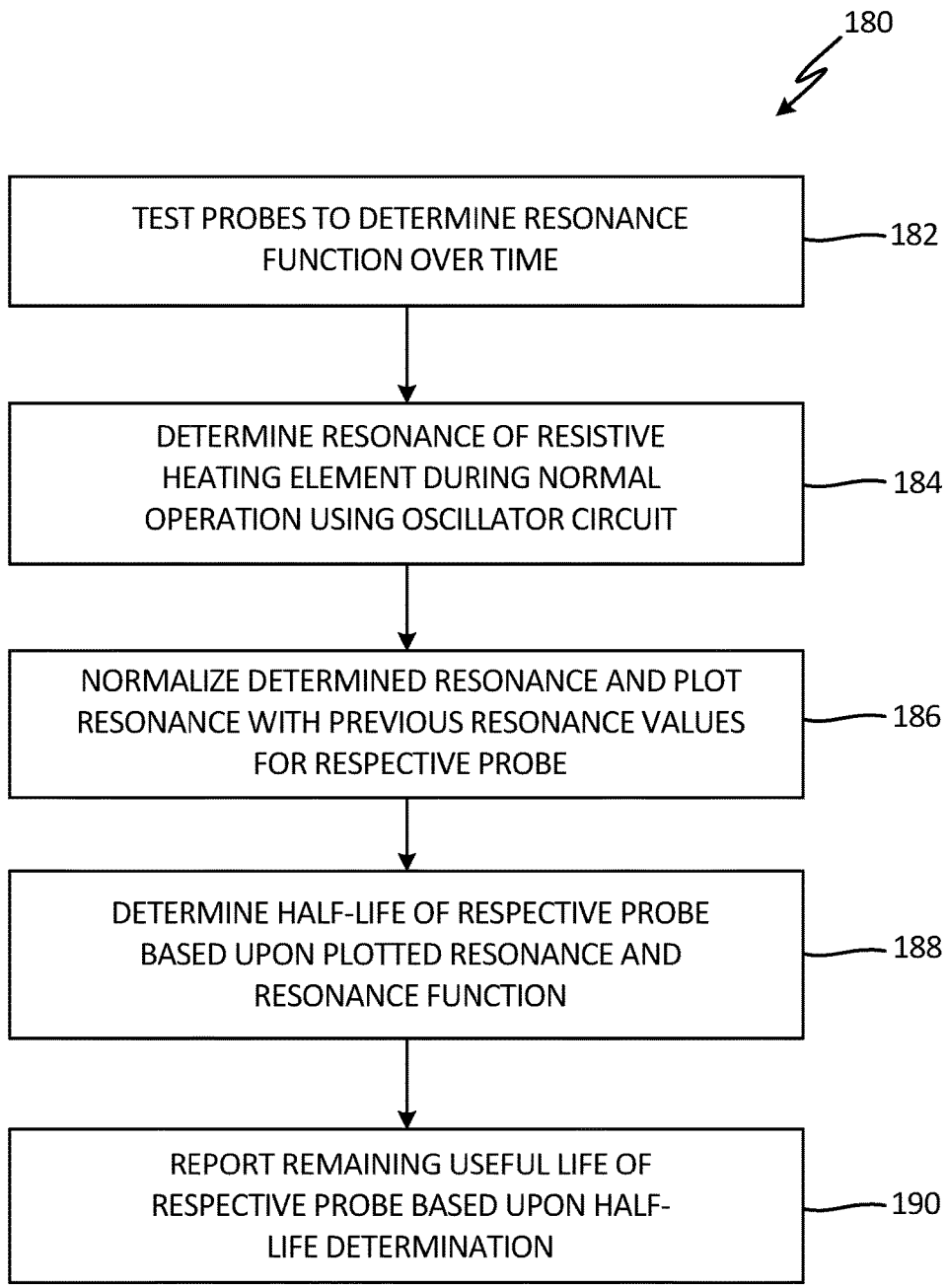
FIG. 12 is a flowchart illustrating a method of determining a remaining useful life of a probe based upon a resonant frequency of a heating element of the probe.

FIG. 12 is a flowchart illustrating method 180 of determining a remaining useful life of probes 12a-12n based upon a resonant frequency of a respective heating element 14. At step 182, an exponential function for a respective probe 12a-12n may be determined, for example, through testing of similar test probes. The exponential function may be similar to that shown in FIG. 6. The test probes may have a test current provided to a respective resistive heating element 14 during a plurality of test cycles to simulate the life of the respective probe 12a-12n. The current may be cycled until failure of each respective probe 12a-12n. The resonant frequency based on the capacitance of each respective heating element 14 may be determined during each cycle, for example, using capacitive measurement circuit 50. Alternatively, an output frequency of oscillator circuit 48 driven by the capacitance of heating element 14 may be determined during each cycle. An exponential function, such as that shown in FIG. 4 or FIG. 6, may be determined based upon the determined resonant or output frequency. This exponential function may then be used for all similar probes 12a-12n during normal probe operation in order to determine a half-life of a respective resistive heating element 14, for example.

At step 184, during normal operation of probes 12a-12n, capacitive measurement circuit 50 may be used to determine a resonant frequency of heating element 14 or ring oscillator circuit 48 may be utilized to determine an output frequency of ring oscillator 48 driven by the capacitance of heating element 14. At step 186, temperature may also be sensed and provided to control and interface circuit 16 using temperature sensor 24. Control and interface circuit 16 may normalize the determined resonant frequency using the sensed temperature. Steps 184 and 186 may be repeated and control and interface circuit 16 may plot the normalized resonant or output frequency over several flights, for example, to establish a curve fit. While theoretical capacitance is not directly affected by temperature, in practice both the capacitance and ring oscillator circuit 48 may be directly affected by temperature. The curve fit may substantially follow the exponential function determined, for example, at step 182. At step 188, the present slope of the determined resonance may be determined based upon the exponential function. This slope may then be utilized to determine the half-life of resistive heating element 14. By knowing the half-life of resistive heating element 14, the remaining useful life of resistive heating element 14 may be determined by control and interface circuit 16, for example.

Once the remaining useful life of resistive heating element 14 is determined by control and interface circuit 16, the remaining useful life may be reported at step 190. This report may be made to the cockpit through avionics 20, or to some other computer system. By reporting the remaining useful life, probes 12a-12n may be replaced prior to breaking down and thus, unnecessary flight delays may be avoided.

Figure 13:
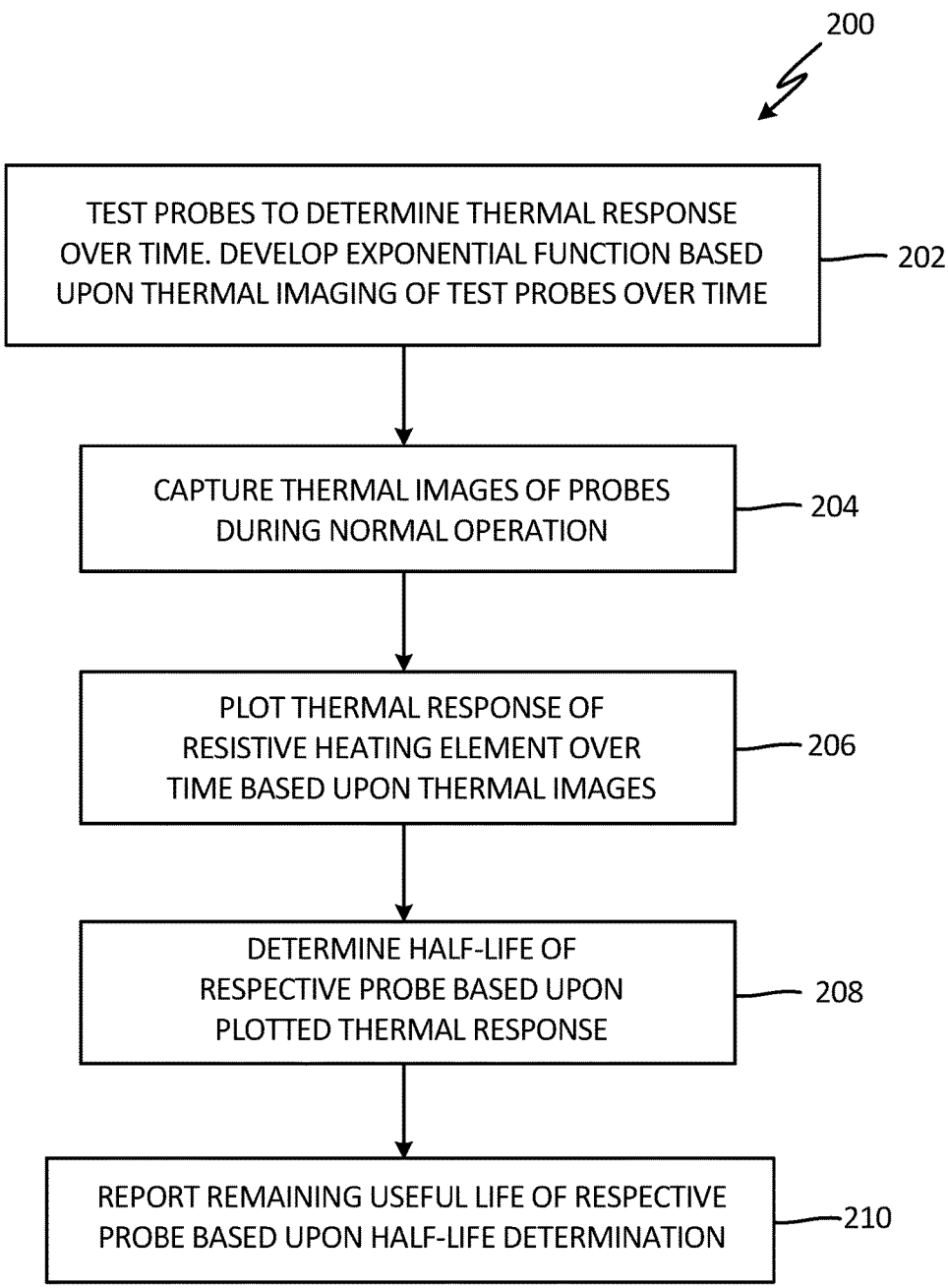
FIG. 13 is a flowchart illustrating a method of determining a remaining useful life of a probe based upon thermal imaging of the probe.

FIG. 13 is a flowchart illustrating method 200 of determining a remaining useful life of probes 12a-12n based upon thermal imaging of a respective heating element 14. At step 202, an exponential function for a respective probe 12a-12n may be determined, for example, through testing of similar test probes. The exponential function may be similar to that shown in FIG. 4. The test probes may have a test current provided to a respective resistive heating element 14 during a plurality of test cycles to simulate the life of the respective probe 12a-12n. The current may be cycled until failure of each respective probe 12a-12n. Thermal images may be taken by thermal imager 28 for each respective heating element 14 each cycle, for example. An exponential function, such as that shown in FIG. 4, may be determined based upon the thermal images. This exponential function may then be used for all similar probes 12a-12n during normal probe operation in order to determine a half-life of a respective resistive heating element 14, for example.

At step 204, during normal operation of probes 12a-12n, thermal imager 28 may be utilized to obtain thermal images of heating element 14. At step 206, temperature may also be sensed and provided to control and interface circuit 16 using temperature sensor 24. Control and interface circuit 16 may normalize the thermal data using the sensed temperature. Control and interface circuit 16 may also normalize the thermal image data to compensate for probe shape and surface emissivity, for example. Steps 204 and 206 may be repeated and control and interface circuit 16 may plot the normalized thermal data over several flights, for example, to establish a curve fit. The curve fit may substantially follow the exponential function determined, for example, at step 202. At step 208, the present slope of the determined thermal data be determined based upon the exponential function. This slope may then be utilized to determine the half-life of resistive heating element 14. By knowing the half-life of resistive heating element 14, the remaining useful life of resistive heating element 14 may be determined by control and interface circuit 16, for example.

Once the remaining useful life of resistive heating element 14 is determined by control and interface circuit 16, the remaining useful life may be reported at step 210. This report may be made to the cockpit through avionics 20, or to some other computer system. By reporting the remaining useful life, probes 12a-12n may be replaced prior to breaking down and thus, unnecessary flight delays may be avoided.

Figure 14:
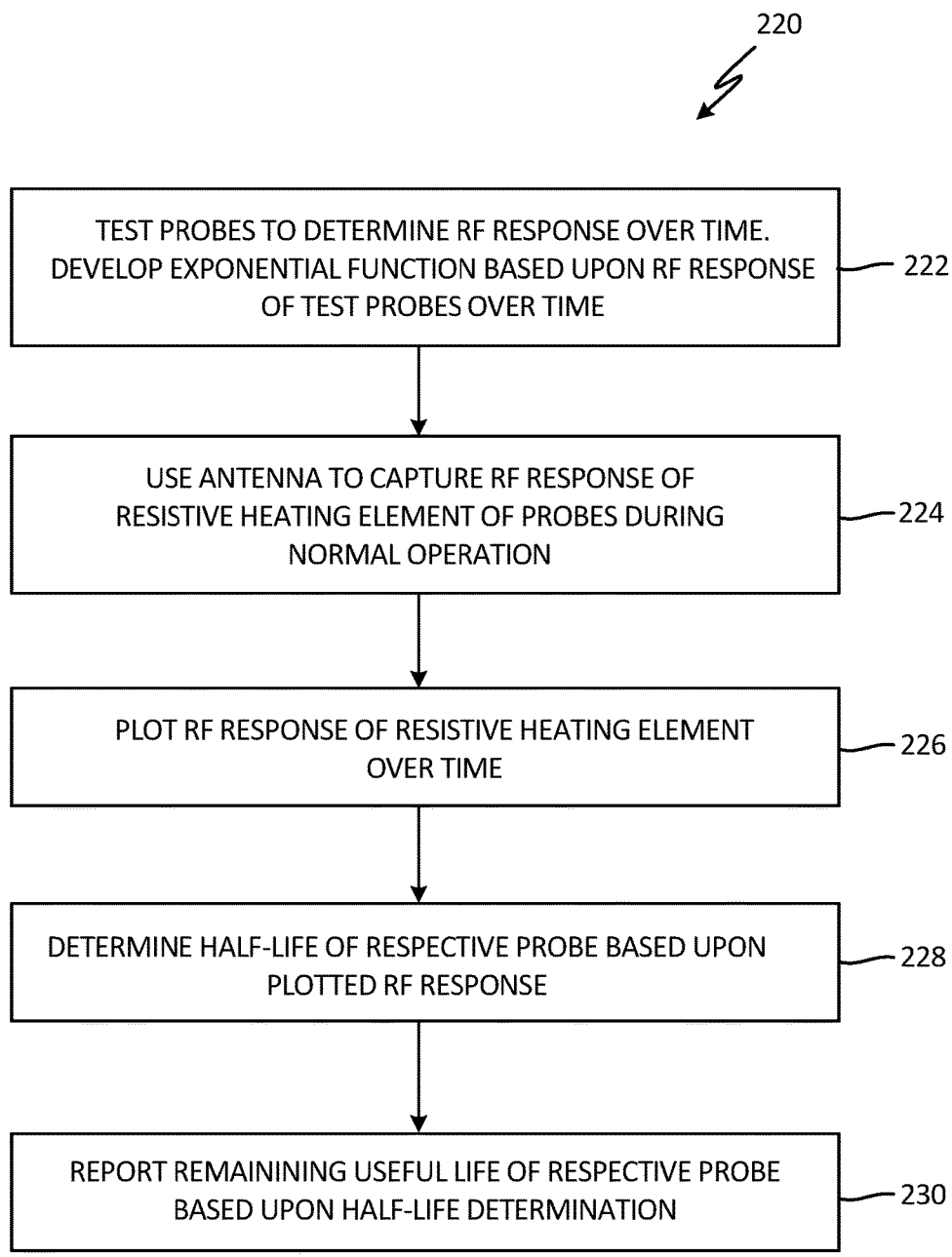
FIG. 14 is a flowchart illustrating a method of determining a remaining useful life of a probe based upon an antenna response of a heater element of the probe.

FIG. 14 is a flowchart illustrating method 220 of determining a remaining useful life of probes 12a-12n based upon an antenna response of a respective heating element 14. At step 222, an exponential function for a respective probe 12a-12n may be determined, for example, through testing of similar test probes. The exponential function may be similar to that shown in FIG. 4. The test probes may have a test current provided to a respective resistive heating element 14 during a plurality of test cycles to simulate the life of the respective probe 12a-12n. The current may be cycled until failure of each respective probe 12a-12n. RF antenna 30 may be utilized during each cycle, for example, to sweep frequencies of RF radiation to heating element 14. An exponential function, such as that shown in FIG. 4, may be determined based upon a detected resonant frequency of heater element 14 in response to the RF radiation from antenna 30 over each cycle. This exponential function may then be used for all similar probes 12a-12n during normal probe operation in order to determine a half-life of a respective resistive heating element 14, for example.

At step 224, during normal operation of probes 12a-12n, RF antenna 30 may be utilized to provide RF radiation to heating element 14. At step 226, control and interface circuit 16 may monitor the S12 parameter of heating element 14 to determine a resonant frequency response of heating element 14 to the RF radiation. In an alternative embodiment, heating element 14 may be energized to provide RF radiation to antenna 30 and control and interface circuit 16 may monitor the S12 parameter of antenna 30 to determine a resonant frequency response of antenna 30.

Steps 224 and 226 may be repeated and control and interface circuit 16 may plot the resonant frequency response over several flights, for example, to establish a curve fit. The curve fit may substantially follow the exponential function determined, for example, at step 222. At step 228, the present slope of the determined RF response may be determined based upon the exponential function. This slope may then be utilized to determine the half-life of resistive heating element 14. By knowing the half-life of resistive heating element 14, the remaining useful life of resistive heating element 14 may be determined by control and interface circuit 16, for example. During steps 224 and 226, the RF response may be normalized to account for, among other things, temperature. This may be accomplished using data from temperature sensor 24, or an estimate temperature based upon data from avionics 20, for example.

Once the remaining useful life of resistive heating element 14 is determined by control and interface circuit 16, the remaining useful life may be reported at step 230. This report may be made to the cockpit through avionics 20, or to some other computer system. By reporting the remaining useful life, probes 12a-12n may be replaced prior to breaking down and thus, unnecessary flight delays may be avoided.

DISCUSSION OF POSSIBLE EMBODIMENTS

The following are non-exclusive descriptions of possible embodiments of the present invention.

A system for an aircraft includes a probe and a control circuit. The probe includes a heater comprising a resistive heating element routed through the probe. An operational voltage is provided to the resistive heating element to provide heating for the probe. The control circuit is configured to determine and monitor a circuit frequency based on an element capacitance between the resistive heating element and a metallic sheath of the heater over time. The control circuit is further configured to determine a remaining useful life of the probe based on the circuit frequency of the resistive heating element over time.

The system of the preceding paragraph can optionally include, additionally and/or alternatively, any one or more of the following features, configurations and/or additional components:

A further embodiment of the foregoing system, wherein the heater further comprises a lead wire and insulation between the lead wire and the metallic sheath.

A further embodiment of any of the foregoing systems, wherein the circuit frequency is a resonance frequency, and wherein the control circuit is configured determine the resonance frequency by sweeping a monitor circuit connected to the element capacitance with a plurality of frequencies and determining the resonance frequency.

A further embodiment of any of the foregoing systems, wherein the circuit frequency is an output frequency of an oscillator circuit, and wherein the output frequency of the oscillator circuit is driven by the element capacitance, and wherein the control circuit is configured to monitor the output frequency over time.

A further embodiment of any of the foregoing systems, wherein the control circuit is configured to store and plot the circuit frequency over a plurality of flights of the aircraft and determine a half-life estimate based on the plot, and wherein the control circuit is configured to determine the remaining useful life based on the half-life estimate.

A further embodiment of any of the foregoing systems, wherein the control circuit is configured to execute an algorithm to determine the remaining useful life of the probe based on the circuit frequency over time.

A further embodiment of any of the foregoing systems, further comprising a temperature sensor configured to sense a temperature of the probe and provide the sensed temperature to the control circuit, wherein the control circuit is configured to normalize the circuit frequency based on the sensed temperature.

A further embodiment of any of the foregoing systems, wherein the control circuit is configured to normalize the circuit frequency based on an estimated temperature of the probe.

A method for determining a remaining useful life of a probe includes providing an operational voltage to a heater of the aircraft probe during a plurality of flights of an aircraft to provide heat for the probe, wherein the heater includes a resistive heating element and a metallic sheath; determining, by a control circuit, a circuit frequency based on an element capacitance between the resistive heating element and the metallic sheath during the plurality of flights; and determining the remaining useful life of the probe based upon the circuit frequency over time.

The method of the preceding paragraph can optionally include, additionally and/or alternatively, any one or more of the following features, configurations and/or additional components:

A further embodiment of the foregoing method, wherein determining, by the control circuit, the circuit frequency includes sweeping a monitor circuit connected to the element capacitance with a plurality of frequencies; and determining a resonance frequency of the monitor circuit, wherein the circuit frequency is the resonance frequency of the monitor circuit.

A further embodiment of any of the foregoing methods, wherein determining, by the control circuit, the circuit frequency includes monitoring an output frequency of an oscillator circuit over the plurality of flights, wherein the output frequency of the oscillator circuit is driven by the element capacitance, and wherein the circuit frequency is the output frequency of the oscillator circuit.

A probe system includes a heater and a control circuit. The heater includes a resistive heating element routed through the probe system. An operational voltage is provided to the resistive heating element to provide heating for the probe system. The control circuit is configured to provide the operational voltage and monitor a circuit frequency based on an element capacitance between the resistive heating element and a metallic sheath of the heater over time. The control circuit is further configured to determine remaining useful life of the probe system based on the circuit frequency.

The probe system of the preceding paragraph can optionally include, additionally and/or alternatively, any one or more of the following features, configurations and/or additional components:

A further embodiment of the foregoing probe system, wherein the heater further comprises a lead wire and insulation between the lead wire and the metallic sheath.

A further embodiment of any of the foregoing probe systems, wherein the circuit frequency is a resonance frequency, and wherein the control circuit is configured determine the resonance frequency by sweeping a monitor circuit connected to the element capacitance with a plurality of frequencies and determining the resonance frequency.

A further embodiment of any of the foregoing probe systems, wherein the circuit frequency is an output frequency of an oscillator circuit, and wherein the output frequency of the oscillator circuit is driven by the element capacitance, and wherein the control circuit is configured to monitor the output frequency over time.

A further embodiment of any of the foregoing probe systems, wherein the control circuit is configured to store and plot the circuit frequency over a plurality of flights of an aircraft and determine a half-life estimate based on the plot, and wherein the control circuit is configured to determine the remaining useful life based on the half-life estimate.

A further embodiment of any of the foregoing probe systems, wherein the control circuit is configured to execute an algorithm to determine the remaining useful life of the probe based on the circuit frequency over time.

A further embodiment of any of the foregoing probe systems, further comprising a temperature sensor configured to sense a temperature of the probe and provide the sensed temperature to the control circuit, wherein the control circuit is configured to normalize the circuit frequency based on the sensed temperature.

A further embodiment of any of the foregoing probe systems, wherein the control circuit is configured to normalize the circuit frequency based on an estimated temperature of the probe.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A system for an aircraft, the system comprising:
a probe that includes a heater comprising a resistive heating element routed through the probe, wherein an operational voltage is provided to the resistive heating element to provide heating for the probe, and wherein the heating element comprises:
a lead wire;
a metallic sheath; and
insulation between the lead wire and the metallic sheath;
a capacitive measurement circuit connected between the lead wire and the metallic sheath and configured to provide an output indicative of an element capacitance between the lead wire and the metallic sheath; and
a control circuit connected to receive the element capacitance and configured to determine and monitor a resonance frequency of the element capacitance over time;
wherein the control circuit is further configured to determine a remaining useful life of the probe based on the resonance frequency of the resistive heating element over time.

2. The system of claim 1, wherein the control circuit is configured to determine the resonance frequency by sweeping the capacitive measurement circuit with a plurality of frequencies.

3. The system of claim 1, wherein the capacitive measurement circuit includes an oscillator circuit, and wherein the resonance frequency is an output frequency of the oscillator circuit, and wherein the output frequency of the oscillator circuit is driven by the element capacitance, and wherein the control circuit is configured to monitor the output frequency over time.

4. The system of claim 1, wherein the control circuit is configured to store and plot the resonance frequency over a plurality of flights of the aircraft and determine a half-life estimate based on the plot, and wherein the control circuit is configured to determine the remaining useful life based on the half-life estimate.

5. The system of claim 1, wherein the control circuit is configured to execute an algorithm to determine the remaining useful life of the probe based on the resonance frequency over time.

6. The system of claim 1, further comprising a temperature sensor configured to sense a temperature of the probe and provide the sensed temperature to the control circuit, wherein the control circuit is configured to normalize the resonance frequency based on the sensed temperature.

7. The system of claim 1, wherein the control circuit is configured to normalize the resonance frequency based on an estimated temperature of the probe.

8. A method for determining a remaining useful life of a probe, the method comprising:
providing an operational voltage to a heater of the aircraft probe during a plurality of flights of an aircraft to provide heat for the probe, wherein the heater includes a resistive heating element that includes a lead wire and a metallic sheath;
determining, by a control circuit, a resonance frequency based on an element capacitance between the lead wire and the metallic sheath during the plurality of flights; and
determining the remaining useful life of the probe based upon the resonance frequency over time.

9. The method of claim 8, wherein determining, by the control circuit, the resonance frequency comprises:
sweeping a monitor circuit connected to the lead wire and the metallic sheath with a plurality of frequencies; and
determining a resonance frequency of the monitor circuit.

10. The method of claim 8, wherein determining, by the control circuit, the resonance frequency comprises:
monitoring an output frequency of an oscillator circuit connected to the lead wire and the metallic sheath over the plurality of flights, wherein the output frequency of the oscillator circuit is driven by the element capacitance, and wherein the resonance frequency is the output frequency of the oscillator circuit.

11. A probe system comprising:
a heater comprising a resistive heating element routed through the probe system, wherein an operational voltage is provided to the resistive heating element to provide heating for the probe system, and wherein the heating element comprises:
a lead wire;
a metallic sheath; and
insulation between the lead wire and the metallic sheath; and
a control circuit configured to provide the operational voltage and monitor a resonance frequency based on an element capacitance between the lead wire and a metallic sheath of the resistive heating element over time;
wherein the control circuit is further configured to determine remaining useful life of the probe system based on the resonance frequency over time.

12. The probe system of claim 11, wherein the control circuit is configured determine the resonance frequency by sweeping a monitor circuit connected to the lead wire and the metallic sheath with a plurality of frequencies.

13. The probe system of claim 11, wherein the resonance frequency is an output frequency of an oscillator circuit connected to the lead wire and the metallic sheath, and wherein the output frequency of the oscillator circuit is driven by the element capacitance, and wherein the control circuit is configured to monitor the output frequency over time.

14. The probe system of claim 11, wherein the control circuit is configured to store and plot the resonance frequency over a plurality of flights of an aircraft and determine a half-life estimate based on the plot, and wherein the control circuit is configured to determine the remaining useful life based on the half-life estimate.

15. The probe system of claim 11, wherein the control circuit is configured to execute an algorithm to determine the remaining useful life of the probe system based on the resonance frequency over time.

16. The probe system of claim 11, further comprising a temperature sensor configured to sense a temperature of the probe system and provide the sensed temperature to the control circuit, wherein the control circuit is configured to normalize the resonance frequency based on the sensed temperature.

17. The probe system of claim 11, wherein the control circuit is configured to normalize the resonance frequency based on an estimated temperature of the probe system.

* * * * *